United States Patent [19]

Stetter et al.

[11] 4,353,915

[45] Oct. 12, 1982

[54] COMBATING PESTS WITH 2-(AZOL-1-YL)-ALDOXIME-CARBAMATES

[75] Inventors: Jörg Stetter, Wuppertal; Bernhard Homeyer, Leverkusen; Ingeborg Hammann, Cologne, all of Fed. Rep. of Germany

[73] Assignee: Bayer Aktiengesellschaft, Leverkusen, Fed. Rep. of Germany

[21] Appl. No.: 869,067

[22] Filed: Jan. 12, 1978

[30] Foreign Application Priority Data

Feb. 4, 1977 [DE] Fed. Rep. of Germany ....... 2704682
Jul. 28, 1977 [DE] Fed. Rep. of Germany ....... 2734107

[51] Int. Cl.³ ................. A01N 47/24; C07D 231/12; C07D 233/61; C07D 249/08
[52] U.S. Cl. .................. 424/269; 424/245; 424/273 R; 424/273 B; 424/273 P; 424/273 N; 548/101; 548/251; 548/253; 548/255; 548/259; 548/260; 548/265; 548/333; 548/337; 548/341; 548/372; 548/376; 548/377; 548/375; 548/378; 548/262
[58] Field of Search ............. 260/308 R; 548/341, 548/262, 326, 375, 378, 377, 372, 255, 333, 259, 260, 265, 337; 424/269, 273 R, 273 B, 273 P, 273 N

[56] References Cited

U.S. PATENT DOCUMENTS 3,478,039 11/1969 Bell ...................... 548/341
3,742,056 6/1973 Henderson .............. 260/308 R
3,818,029 6/1974 Regel et al. ............ 548/343

*Primary Examiner*—Alton D. Rollins
*Attorney, Agent, or Firm*—Sprung, Horn, Kramer & Woods

[57] ABSTRACT

2-(Azol-1-yl)-aldoxime-carbamates of the formula

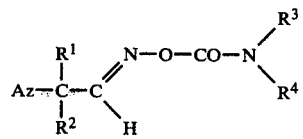

wherein
$R^1$ and $R^2$ each independently is alkyl or together form an alkylene bridge,
$R^3$ is hydrogen or alkyl,
$R^4$ is hydrogen, alkyl, alkenyl, alkynyl, halogenoalkyl, halogenoalkenyl, alkoxyalkyl or alkylthioalkyl, and
Az is azolyl, which possess arthropodicidal and nematicidal properties.

9 Claims, No Drawings

COMBATING PESTS WITH 2-(AZOL-1-YL)-ALDOXIME-CARBAMATES

The present invention relates to and has for its objects the provision of particular new 2-(azol-1-yl)-aldoxime-carbamates which possess arthropodicidal and nematicidal properties, active compositions in the form of mixtures of such compounds with solid and liquid dispersible carrier vehicles, and methods for producing such compounds, and for using such compounds in a new way especially for combating pests, e.g. arthropods and nematodes, with other and further objects becoming apparent from a study of the within specification and accompanying examples.

It has already been disclosed that certain 2,2-dimethylpropan-aldoxime carbamates, for example 3-hydroxy-2,2-dimethyl-propanaldoxime N-methylcarbamate, possess good insecticidal properties (see German Offenlegungsschrift (German Published Specification) 2,111,156). However, their action is not always satisfactory, in particular when low application amounts are used.

In addition, it has already been disclosed that certain α-cyanooxime carbamates, for example 1-cyano-2-methylpropanaldoxime N-methylcarbamate and 1-cyano-butanaldoxime N-methylcarbamate, possess pesticidal, in particular insecticidal and nematicidal, properties (see German Offenlegungsschrift (German Published Specification) 1,567,142). Their action is also not always completely satisfactory, in particular when low application concentrations are used.

The present invention now provides, as new compounds, the β-azolyl-aldoxime carbamates of the general formula $$\begin{array}{c} R^1 \\ | \\ Az-C-C \\ | \quad \diagdown \\ R^2 \quad H \end{array} \begin{array}{c} N-O-CO-N \diagup R^3 \\ \diagdown R^4 \end{array} \quad (I)$$

in which
R$^1$ and R$^2$, which may be identical or different, each represent alkyl or R$^1$ and R$^2$ together represent an alkylene bridge,
R$^3$ represents hydrogen or alkyl,
R$^4$ represents hydrogen, alkyl, alkenyl, alkynyl, halogenoalkyl, halogenoalkenyl, alkoxyalkyl or alkylthioalkyl and
Az represents an optionally substituted azolyl radical, in the form of the free bases, their salts or metal complexes.

Preferably, R$^1$ and R$^2$, which may be identical or different, each represent straight-chain or branched alkyl with 1 to 4 carbon atoms or R$^1$ and R$^2$ together represent a tetramethylene, pentamethylene or hexamethylene bridge; R$^3$ represents hydrogen or straight-chain or branched alkyl with 1 to 4 carbon atoms; R$^4$ represents hydrogen, straight-chain or branched alkyl with 1 to 12 carbon atoms, alkenyl or alkynyl with 2 to 4 carbon atoms in each case, halogenoalkyl with up to 2 carbon atoms and up to 5 halogen atoms (especially fluorine and chlorine atoms, trifluoromethyl being mentioned as an example of such halogenoalkyl), halogenoalkenyl with up to 3 carbon atoms and up to 5 halogen atoms (especially fluorine and chlorine atoms) or alkoxyalkyl or alkylthioalkyl with up to 2 carbon atoms in each alkyl part; and Az represents a pyrazol-1-yl, imidazol-1-yl, 1,2,4-triazol-1-yl, 1,2,3-triazol-1-yl, 1,3,4-triazol-1-yl, 1,2,5-triazol-1-yl, indazol-1-yl, benzimidazol-1-yl or benztriazol-1-yl radical which optionally carries one or more substituents selected from halogen (especially fluorine, chlorine and bromine), alkyl with 1 to 4 carbon atoms, halogenoalkyl with up to 2 carbon atoms and up to 5 halogen atoms (especially fluorine and chlorine atoms, trifluoromethyl being mentioned as an example of such halogenalkyl), alkoxy and alkylthio with up to 4 carbon atoms in each case, cyano and nitro.

The compounds of the formula (I) can exist in the syn form or in the anti form; they are predominantly obtained as mixtures of both forms.

Surprisingly, the β-azolyl-aldoxime carbamates according to the invention possess a better insecticidal, soil-insecticidal, acaricidal and nematicidal action than the aldoxime carbamates previously known, such as 3-hydroxy-2,2-dimethyl-propanaldoxime N-methylcarbamate, 1-cyano-2-methyl-propanaldoxime N-methylcarbamate and 1-cyanobutanaldoxime N-methylcarbamate, which are the most closely related compounds chemically and from the point of view of their activity. They thus represent an enrichment of the art.

The invention also provides a process for the preparation of a β-azolyl-aldoxime carbamate of the formula (I) in which a β-azolyl-aldoxime of the general formula $$\begin{array}{c} R^1 \\ | \\ Az-C-C \\ | \quad \diagdown \\ R^2 \quad H \end{array} \begin{array}{c} N-OH, \\ \end{array} \quad (II)$$

in which R$^1$, R$^2$ and Az have the meanings stated above,
(a) is reacted with an isocyanate of the general formula $$R^4\text{-N}=C=O \quad (III),$$

in which R$^4$ has the meaning stated above, in the presence of a diluent and optionally in the presence of a catalyst, or
(b) is reacted with a carbamoyl halide of the general formula $$\text{Hal}-CO-N \diagup_{R^4}^{R^3}, \quad (IV)$$

in which
R$^3$ and R$^4$ have the meanings stated above and
Hal represents fluorine or chlorine,
optionally in the presence of a diluent and of an acid-binding agent, or
(c), provided R$^3$ and R$^4$ are to denote hydrogen, is reacted with an alkali metal cyanate of the general formula $$\text{M-OCN} \quad (V),$$

in which M represents sodium, potassium or ammonium, in the presence of an acid and of a diluent.

If 2-methyl-1-oximino-2-imidazol-1-yl-propane and methyl isocyanate are used as starting materials in process variant (a), the course of the reaction can be represented by the following equation:

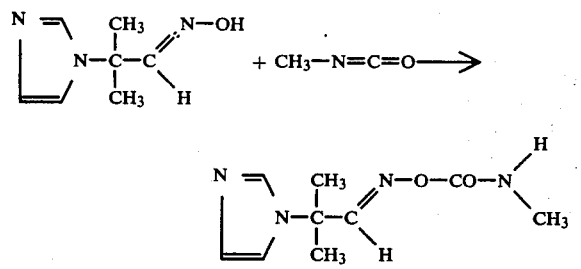

If 2-methyl-1-oximino-2-(1,2,4-triazol-1-yl)-propane and dimethylcarbamoyl chloride are used as starting materials in process variant (b), the course of the reaction can be represented by the following equation:

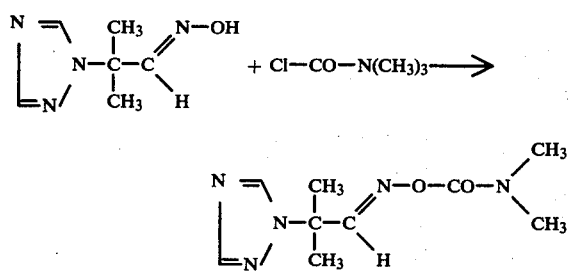

If 2-methyl-1-oximino-2-pyrazol-1-yl-propane and sodium cyanate in hydrochloric acid are used as starting materials in process variant (c), the course of the reaction can be represented by the following equation:

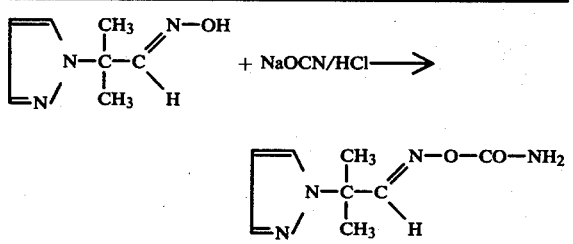

Examples of starting materials of the formula (II) which may be mentioned are: 2-methyl-1-oximino-2-pyrazol-1-yl-propane, 2-methyl-1-oximino-2-(4-chloropyrazol-1-yl)-propane, 2-methyl-1-oximino-2-(4-bromopyrazol-1-yl)-propane, 2-methyl-1-oximino-2-(3-methoxypyrazol-1-yl)-propane, 2-methyl-1-oximino-2-(3-methylpyrazol-1-yl)-propane, 2-methyl-1-oximino-2-imidazol-1-yl-propane, 2-methyl-1-oximino-2-(2-bromoimidazol-1-yl)-propane, 2-methyl-1-oximino-2-(2-methylimidazol-1-yl)-propane, 2-methyl-1-oximino-2-(4-trifluoromethylimidazol-1-yl)-propane, 2-methyl-1-oximino-2-(4-nitroimidazol-1-yl)-propane, 2-methyl-1-oximino-2-(5-methyl-4-nitroimidazol-1-yl)-propane, 2-methyl-1-oximino-2-(2,4,5-tribromoimidazol-1-yl)-propane, 2-methyl-1-oximino-2-(1,2,4-triazol-1-yl)-propane, 2-methyl-1-oximino-2-(5-methyl-1,2,4-triazol-1-yl)-propane, 2-methyl-1-oximino-2-(3,5-dimethyl-1,2,4-triazol-1-yl)-propane, 2-methyl-1-oximino-2-(3-methyl-1,2,4-triazol-1-yl)-propane, 2-methyl-1-oximino-2-(3-1,2,4-triazol-1-yl)-propane, 2-methyl-1-oximino-2-(3-methylthio-1,2,4-triazol-1-yl)-propane, 2-methyl-1-oximino-2-(3-methyl-5-methylthio-1,2,4-triazol-1-yl)-propane, 2-methyl-1-oximino-2-(5-methyl-3-methylthio-1,2,4-triazol-1-yl)-propane, 2-methyl-1-oximino-2-(3-bromo-1,2,4-triazol-1-yl)-propane, 2-methyl-1-oximino-2-(3-chloro-1,2,4-triazol-1-yl)-propane, 2-methyl-1-oximino-2-(1,2,3-triazol-1-yl)-propane, 2-methyl-1-oximino-2-(1,3,4-triazol-1-yl)-propane, 2-methyl-1-oximino-2-(indazol-1-yl)-propane, 2-methyl-1-oximino-2-(benzimidazol-1-yl)-propane, 2-methyl-1-oximino-2-(benztriazol-1-yl)-propane, 2-methyl-1-oximino-2-pyrazol-1-yl-butane, 2-methyl-1-oximino-2-imidazol-1-yl-butane, 2-methyl-1-oximino-2-(1,2,4-triazol-1-yl)-butane, 2-ethyl-1-oximino-2-pyrazol-1-yl-butane, 2-ethyl-1-oximino-2-imidazol-1-yl-butane, 2-ethyl-1-oximino-2-(1,2,4-triazol-1-yl)-butane, 2,2-tetramethylene-1-oximino-2-pyrazol-1-yl-ethane, 2,2-tetramethylene-1-oximino-2-imidazol-1-yl-ethane, 2,2-tetramethylene-1-oximino-2-(1,2,4-triazol-1-yl)-ethane, 2,2-pentamethylene-1-oximino-2-pyrazol-1-yl-ethane, 2,2-pentamethylene-1-oximino-2-imidazol-1-yl-ethane, 2,2-pentamethylene-1-oximino-2-(1,2,4-triazol-1-yl)-ethane, 2,2-hexamethylene-1-oximino-2-pyrazol-1-yl-ethane, 2,2-hexamethylene-1-oximino-2-imidazol-1-yl-ethane and 2,2-hexamethylene-1-oximino-2-(1,2,4-triazol-1-yl)-ethane.

The β-azolyl-aldoximes of the formula (II) have not hitherto been described in the literature. They can be prepared by reacting dimeric nitroso-halides of the general formula

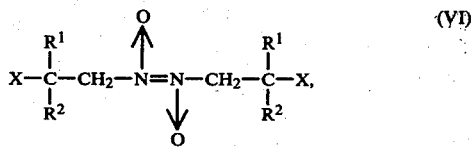

in which
R$^1$ and R$^2$ have the meanings stated above and
X represents halogen, in particular chlorine, with azoles of the general formula Az-H (VII), in which Az has the meaning stated above,
in the presence of an organic solvent, for example acetone, and in the presence of an acid-binding agent, for example potassium carbonate, at temperatures between 30° and 100° C. The compounds of the formula (II) are isolated in the generally customary manner.

Dimeric nitroso-halides of the formula (VI) are disclosed in U.S. Pat. No. 3,217,037. They can all be easily prepared by the processes described therein, by reacting the corresponding olefins with nitrosyl halides, for example nitrosyl chloride.

Examples of starting materials of the formula (III) which may be mentioned are: methyl isocyanate, ethyl isocyanate, i-propyl isocyanate, t-butyl isocyanate, heptyl isocyanate, dodecyl isocyanate, allyl isocyanate, propargyl isocyanate, trifluoromethyl isocyanate, chloromethyl isocyanate, chloroethyl isocyanate, trichlorovinyl isocyanate, methoxymethyl isocyanate, ethoxymethyl isocyanate and methoxyethyl isocyanate.

The isocyanates of the formula (III) are known and can be prepared by generally customary and known processes, for example by reacting amines with phosgene and subsequently heating the products. These processes are known from the general textbooks of organic chemistry.

Examples of starting materials of the formula (IV) which may be mentioned are: methylcarbamoyl chloride, dimethylcarbamoyl chloride, methylethylcarbamoyl chloride, allylmethylcarbamoyl chloride, methoxymethyl-methylcarbamoyl chloride, methyl-trifluoromethylcarbamoyl chloride and ethylvinylcarbamoyl chloride.

The carbamoyl halides of the formula (IV) are known and can be prepared by generally customary and known processes, for example by reacting amines with phosgene. These processes are known from the general textbooks of organic chemistry.

Preferred salts of the compounds of the formula (I) are—from the standpoint of toxicity—salts with physiologically acceptable acids, especially hydrogen halide acids (for example hydrobromic acid and, in particular, hydrochloric acid), phosphoric acid, nitric acid, and monofunctional and bifunctional carboxylic acids, hydroxycarboxylic acids and sulphonic acids (for example acetic acid, maleic acid, succinic acid, fumaric acid, tartaric acid, citric acid, salicylic acid, sorbic acid, lactic acid and 1,5-naphthalene-disulphonic acid).

The salts of the compounds of the formula (I) can be obtained in a simple manner by customary salt formation methods, for example by dissolving the base in ether, for example diethyl ether, and adding the acid, for example nitric acid, and can be isolated in a known manner, for example by filtration, and optionally purified.

Possible complexes of the compounds of the formula (I) are complexes with metal salts. For this there may be mentioned, as preferred, metals of the main groups II to IV and of the sub-groups I, II and IV to VIII, in particular copper, zinc, manganese, magnesium, tin, iron and nickel. Preferred salts are salts with physiologically acceptable acids, especially hydrogen halide acids (for example hydrochloric acid and hydrobromic acid), phosphoric acid, nitric acid and sulphuric acid.

The metal complexes of the compounds of the formula (I) can be obtained in a known manner by customary processes, for example by dissolving the metal salt in alcohol, for example ethanol, and adding the solution to the base. They can be isolated in a known manner, for example by filtration, and optionally purified by recrystallization.

Preferred diluents for the reaction according to process variant (a) are inert organic solvents, especially ketones, such as diethyl ketone and, in particular, acetone and methyl ethyl ketone; nitriles, such as propionitrile and, in particular, acetonitrile; alcohols, such as ethanol or isopropanol; ethers, such as tetrahydrofuran or dioxane; formamides, such as, in particular, dimethylformamide; and halogenated hydrocarbons, such as methylene chloride, carbon tetrachloride or chloroform.

Preferred catalysts which can be used in process variant (a) are tertiary bases, such as triethylamine and pyridine, and organotin compounds, such as dibutyl tin dilaurate (Desmorapid).

The reaction temperatures in carrying out process variant (a) can be varied within a relatively wide range. In general, the reaction is carried out at from 0° to 100° C., preferably from 20° to 85° C.

In carrying out process variant (a), 1 to 2 moles of isocyanate of the formula (III) are preferably employed per mole of the compound of the formula (II). In order to isolate the compounds of the formula (I), the solvent is distilled off and the residue is worked up by customary methods.

Preferred diluents for carrying out the reaction according to process variant (b) are inert organic solvents, especially the solvents listed in connection with process variant (a).

If the reaction according to process variant (b) is carried out in the presence of an acid-binding agent, any of the inorganic and organic acid acceptors which can be customarily used may be added. These include, preferably, alkali metal carbonates, such as, for example, sodium carbonate, potassium carbonate and sodium bicarbonate, and furthermore lower tertiary alkylamines, cycloalkylamines or arylalkylamines, such as, for example, triethylamine, N,N-dimethylbenzylamine, dicyclohexylmethylamine and also pyridine and diazabicyclooctane.

The reaction temperatures in process variant (b) can be varied within a relatively wide range. In general, the reaction is carried out at from 0° to 100° C., preferably at from 0° to 85° C.

In carrying out process variant (b), 1 to 2 moles of carbamoyl chloride of the formula (IV) and 1 to 2 moles of acid-binding agent are preferably employed per mole of the compound of the formula (II). The compounds of the formula (I) are isolated in a generally customary and known manner.

Preferred diluents for the reaction according to process variant (c) are inert organic solvents or their mixtures with water. The preferred inert solvents include the solvents listed in connection with process variant (a).

The reaction temperatures in carrying out process variant (c) can be varied within a relatively wide range. In general, the reaction is carried out at from 0° to 50° C., preferably from 0° to 30° C.

In carrying out process variant (c), 1 to 2 moles of cyanate of the formula (V) are preferably employed per mole of the compound of the formula (II). In order to isolate the compounds, the organic phase is separated off, the solvent is distilled off and the residue is worked up by customary methods.

Examples of particularly active compounds according to the invention are the following: 2-imidazol-1-yl-2-methyl-1-dimethylcarbamoyloximino-propane, 2-(2-methylimidazol-1-yl)-2-methyl-1-dimethylcarbamoyloximino-propane, 2-(1,2,4-triazol-1-yl)-2-methyl-1-dimethylcarbamoyloximino-propane, 2-(1,2,3-triazol-1-yl)-2-methyl-1-methylcarbamoyloximino-propane, 2-(1,2,5-triazol-1-yl)-2-methyl-1-methylcarbamoyloximino-propane, 2-(3-chloro-1,2,4-triazol-1-yl)-2-methyl-1-methylcarbamoyloximino-propane, 2-(3-fluoro-1,2,4-triazol-1-yl)-2-methyl-1-methylcarbamoyloximino-propane, 2-(3-methoxy-1,2,4-triazol-1-yl)-2-methyl-1-methylcarbamoyloximino-propane, 2-(3-nitro-1,2,4-triazol-1-yl)-2-methyl-1-methylcarbamoyloximino-propane, 2-(3-trifluoromethyl-1,2,4-triazol-1-yl)-2-methyl-1-methylcarbamoyloximino-propane, 2-(3-cyano-1,2,4-triazol-1-yl)-2-methyl-1-methylcarbamoyloximino-propane, 2-(4-nitro-5-methyl-imidazol-1-yl)-2-methyl-1-methylcarbamoyloximino-propane, 2-(4-nitroimidazol-1-yl)-2-methyl-1-methylcarbamoyloximino-propane, 2-(3-methyl-pyrazol-1-yl)-2-methyl-1-methylcarbamoyloximino-propane, 2-(3-methylmercapto-pyrazol-1-yl)-2-methyl-1-methylcarbamoyloximino-propane, 2-(3,4,5-tribromo-pyrazol-1-yl)-2-methyl-1-methylcarbamoyloximino-propane, 2-(4-chloro-pyrazol-1-yl)-2-methyl-1-methylcarbamoyloximino-propane, 2-(4-bromopyrazol-1-yl)-2-methyl-1-methylcarbamoyloximino-propane, 2-(4-fluoropyrazol-1-yl)-2-methyl-1-methylcarbamoyloximino-propane, 2-(1,2,4-triazol-1-yl)-2-methyl-1-methylcarbamoyloximino-butane, 2-(1,2,3-triazol-1-yl)-2-methyl-1-methylcarbamoyloximino-butane, 2-(pyrazol-1-yl)-2-methyl-1-methylcarbamoyloximino-butane and 2-(1,2,4-triazol-1-yl)-2,2-pentamethylene-1-methylcarbamoyloximino-ethane and their salts and metal complexes. Other active compounds are mentioned in the preparative examples later in this text.

The active compounds are well tolerated by plants, have a favorable level of toxicity to warm-blooded animals, and can be used for combating arthropod pests, especially insects and acarids, or nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp.; *Phorodon humuli, Rhopalosiphum padi,* Empoasca spp.; *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Fuxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing an active ingredient a compound of the present invention in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is illustrated in the following examples:

EXAMPLE 1

Preparation of the starting materials of the formula (II)

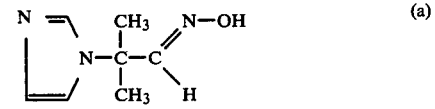

28 g (0.12 mole) of dimeric 2-chloro-2-methyl-1-nitrosopropane were added in portions to a mixture of 17.1 g (0.25 mol) of imidazole and 34.5 g (0.25 mole) of potassium carbonate in 250 ml of acetone, while stirring. The mixture was then heated under reflux for 5 hours. It was allowed to cool and filtered and the filtrate was concentrated by distilling off the solvent. The crystalline residue was recrystallized from ethyl acetate. This gave 19 g (52% of theory) of 2-imidazol-1-yl-2-methyl-1-oximinopropane of melting point 117°–120° C.

The compounds listed in Table 1 which follows were obtained analogously.

TABLE 1

| Compound | $R^1$ | $R^2$ | Az | Melting point (°C.) |
|---|---|---|---|---|
| b | $CH_3$ | $CH_3$ | (triazolyl) | 132–134 |

TABLE 1-continued $$Az-\underset{R^2}{\underset{|}{C}}-C\underset{H}{\overset{N-OH}{\diagup}} \quad (II)$$

| Compound | R¹ | R² | Az | Melting point (°C.) |
|----------|-----|-----|-----|---------------------|
| c | CH₃ | CH₃ | (imidazol-1-yl) | 105–110 |
| d | CH₃ | CH₃ | (4-methyl-1,2,4-triazol-1-yl) | 72–90 |
| e | CH₃ | CH₃ | (4-methylimidazol-1-yl) | 85–92 |
| f | CH₃ | CH₃ | (3-methylthio-1,2,4-triazol-1-yl) | 108–117 |
| g | CH₃ | CH₃ | (3-methylthio-5-methyl-1,2,4-triazol-1-yl) | viscous oil |
| h | CH₃ | CH₃ | (3,5-dimethyl-1,2,4-triazol-1-yl) | 154–157 |

EXAMPLE 2

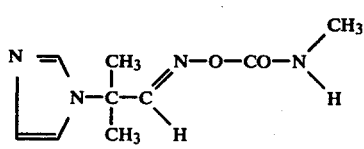
(1)

5.1 g (0.09 mol) of methyl isocyanate were added to 7 g (0.045 mol) of 2-imidazol-1-yl-2-methyl-1-oximino-propane in 50 ml of methylene chloride and the mixture was stirred for 8 hours at room temperature. The volatile constituents were then distilled off in vacuo and the crystalline residue was rinsed with diisopropyl ether. This gave 9 g (95% of theory) of 2-imidazol-1-yl-2-methyl-1-methylcarbamoyloximinopropane of melting point 92°–96° C.

EXAMPLE 3

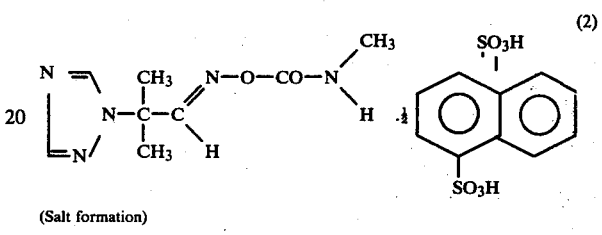
(2)

(Salt formation)

10.5 g (0.05 mol) of 2-methyl-1-methylcarbamoyloximino-2-(1,2,4-triazol-1-yl)-propane (Compound 4; preparation analogus to that of Example 2) were dissolved in 80 ml of acetone and a solution of 10 g of 1,5-naphthalenedisulphonic acid in 30 ml of acetone was added. The reaction product, which precipitated after a short time, was filtered off, washed with acetone and dried. This gave 16.3 g (92% of theory) of 2-methyl-1-methylcarbamoyloximino-2-(1,2,4-thriazol-1-yl)-propane 1,5-naphthalenedisulphonate of melting point 165° C. (sintered).

EXAMPLE 4

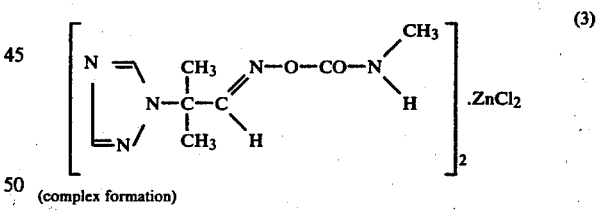
(3)

(complex formation)

10.5 g (0.05 mol) of 2-methyl-1-methylcarbamoyloximino-2-(1,2,4-triazol-1-yl)-propane (Compound 4; preparation analogous to that of Example 2) were dissolved in 50 ml of methylene chloride and a solution of 3.4 g (0.025 mol) of zinc dichloride in 80 ml of methylene chloride was added dropwise. After stirring the mixture for several hours at room temperature, the precipitate formed was filtered off and dried. This gave 9.4 g (74% of theory) of bis-[2-methyl-1-methylcarbamoyloximino-2-(1,2,4-triazol-1-yl)-propane]-zinc(II) chloride of melting point 140° C.

The compounds listed in Table 2 which follows were obtained analogously.

TABLE 2

$$\text{Az}-\underset{R^2}{\overset{R^1}{C}}-\underset{H}{C}=N-O-CO-N\underset{R^4}{\overset{R^3}{\diagdown}}$$ (I)

| Compound | R¹ | R² | R³ | R⁴ | Az | Melting point (°C.) |
|---|---|---|---|---|---|---|
| 4 | CH₃ | CH₃ | H | CH₃ | 1,2,4-triazol-1-yl | viscous oil |
| 5 | CH₃ | CH₃ | CH₃ | H | pyrazol-1-yl | viscous oil |
| 6 | CH₃ | CH₃ | H | CH₃ | 3-methyl-1,2,4-triazol-1-yl | 97–103 |
| 7 | CH₃ | CH₃ | H | CH₃ | 2-methylimidazol-1-yl | viscous oil |
| 8 | CH₃ | CH₃ | H | CH₃ | 3-methylthio-1,2,4-triazol-1-yl | 94–96 |
| 9 | CH₃ | CH₃ | H | CH₃ | 3-methyl-5-methylthio-1,2,4-triazol-1-yl | viscous oil |
| 10 | CH₃ | CH₃ | H | CH₃ | 3,5-dimethyl-1,2,4-triazol-1-yl | viscous oil |
| 11 | CH₃ | CH₃ | H | CH₃OCH₂— | pyrazol-1-yl | viscous oil |
| 12 | CH₃ | CH₃ | H | CH₃ | 1,2,3-triazol-1-yl | 103–105 |
| 13 | CH₃ | CH₃ | H | CH₃ | 5-methylthio-1,2,3-triazol-1-yl | viscous oil |

TABLE 2-continued $$Az-\underset{R^2}{\overset{R^1}{C}}-\underset{H}{C}=N-O-CO-N\underset{R^4}{\overset{R^3}{<}} \quad (I)$$

| Compound | $R^1$ | $R^2$ | $R^3$ | $R^4$ | Az | Melting point (°C.) |
|---|---|---|---|---|---|---|
| 14 | $CH_3$ | $CH_3$ | H | $CH_3$ | 1,2,4-triazolyl | viscous oil (.$H_3PO_4$) |
| 15 | $CH_3$ | $CH_3$ | H | $CH_3$ | 1,2,4-triazolyl | viscous oil (.½ COOH–COOH) |
| 16 | $CH_3$ | $CH_3$ | H | $CH_3$ | 1,2,4-triazolyl | 48–53 (.½ $CuCl_2$) |
| 17 | $CH_3$ | $CH_3$ | H | $CH_3$ | 1,2,4-triazolyl | (.HCl) |
| 18 | $CH_3$ | $CH_3$ | H | $CH_3$ | 1,2,4-triazolyl | (.$HNO_3$) |
| 19 | $CH_3$ | $CH_3$ | H | $CH_3$ | 1,2,4-triazolyl | (.$H_2SO_4$) |
| 20 | $CH_3$ | $CH_3$ | H | $CH_3$ | 1,2,4-triazolyl | (.½ HC(COOH)–HC(COOH)) |
| 21 | $CH_3$ | $CH_3$ | H | $CH_3$ | 1,2,4-triazolyl | (.$CH_3$–C$_6$H$_4$–$SO_3H$) |
| 22 | $CH_3$ | $CH_3$ | H | $CH_3$ | 1,2,4-triazolyl | 100 (.$CH_3$–$SO_3H$) |
| 23 | $CH_3$ | $CH_3$ | H | $CH_3$ | 1,2,4-triazolyl | (.$C_4F_9$–$SO_3H$) |
| 24 | $CH_3$ | $CH_3$ | H | $CH_3$ | 1,2,4-triazolyl | (.naphthalene-1,5-disulfonic acid) |

TABLE 2-continued $$Az-\underset{R^2}{\overset{R^1}{C}}-\underset{H}{C}=N-O-CO-N\underset{R^4}{\overset{R^3}{\diagdown}} \quad (I)$$

| Compound | R¹ | R² | R³ | R⁴ | Az | Melting point (°C.) |
|---|---|---|---|---|---|---|
| 25 | CH₃ | CH₃ | H | CH₃ | -N⟨N=⟨ ⟩N⟩ | (.½ benzene-1,3-di-SO₃H) |
| 26 | CH₃ | CH₃ | H | CH₃ | -N⟨N=⟨ ⟩N⟩ | (.½ naphthalene-2,6-di-SO₃H) |
| 27 | CH₃ | CH₃ | H | CH₃ | -N⟨N=⟨ ⟩N⟩ | (.½ 2-hydroxybenzenesulfonic acid) |
| 28 | CH₃ | CH₃ | H | CH₃ | -N⟨N=⟨ ⟩N⟩ | (.½ 2-carboxybenzenesulfonic acid) |
| 29 | CH₃ | CH₃ | H | CH₃ | -N⟨N=⟨ ⟩N⟩ | (.½ SnCl₄) |
| 30 | CH₃ | CH₃ | H | CH₃ | -N⟨N=⟨ ⟩N⟩ | (.½ MgCl₂) |
| 31 | CH₃ | CH₃ | H | CH₃ | -N⟨N=⟨ ⟩N⟩ | (.½ MnCl₂) |

The insecticidal, acaricidal and nematicidal activity of the compounds of this invention is illustrated by the following examples wherein the compounds according to the present invention are each identified by the number (given in brackets) from the preparative examples hereinabove.

The known comparison compounds are identified as follows:

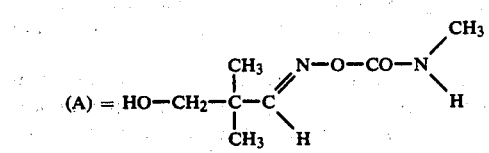

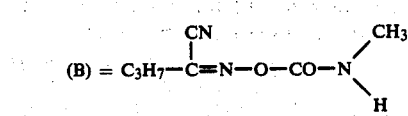

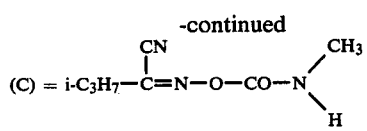

EXAMPLE 5

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

TABLE 3

| Active compound | Nematicides (*Meloidogyne incognita*) Degree of destruction in % at an active compound concentration of 5 ppm |
| --- | --- |
| (A) | 0 |
| (4) | 100 |
| (1) | 100 |
| (6) | 100 |
| (8) | 100 |

EXAMPLE 6

Root-systemic action
Test animal: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test animals after 7 days. After a further 2 days, the results were evaluated by counting or estimating the dead animals. The root-systemic action of the active compound was deduced from the destruction data. It was 100% when all of the test animals had been killed and 0% when just as many test insects were still alive as in the case of the untreated control.

The active compounds, the amounts used and the results can be seen from the following table:

TABLE 4

| Active compound | Root-systemic action (*Myzus persicae*) Destruction in % at an active compound concentration of 20 ppm |
| --- | --- |
| (A) | 0 |
| (4) | 100 |
| (5) | 100 |

TABLE 4-continued

| Active compound | Root-systemic action (*Myzus persicae*) Destruction in % at an active compound concentration of 20 ppm |
| --- | --- |
| (6) | 100 |

EXAMPLE 7

Root-systemic action
Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test animals after 7 days. After a further 2 days, the results were evaluated by counting or estimating the dead animals. The root-systemic action of the active compound was deduced from the destruction data. It was 100% when all of the test animals had been killed and 0% when just as many test insects were still alive as in the case of the untreated control.

The active compounds, the amounts used and the results can be seen from the following table:

TABLE 5

| Active compound | Root-systemic action (*Phaedon cochleariae* larvae) Degree of destruction in % at an active compound concentration of 20 ppm |
| --- | --- |
| (A) | 0 |
| (4) | 100 |
| (5) | 100 |
| (6) | 100 |

EXAMPLE 8

Phaedon larvae test
Solvent: 3 parts by weight of dimethyl formamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

TABLE 6

| | (Insects which damage plants) Phaedon larvae test | |
|---|---|---|
| Active compounds | Active compound concentration in % | Degree of destruction in % after 3 days |
| (B) | 0.1 | 100 |
| | 0.01 | 0 |
| (C) | 0.1 | 100 |
| | 0.01 | 0 |
| (A) | 0.1 | 80 |
| | 0.01 | 0 |
| (5) | 0.1 | 100 |
| | 0.01 | 100 |
| (4) | 0.1 | 100 |
| | 0.01 | 100 |
| (6) | 0.1 | 100 |
| | 0.01 | 100 |

EXAMPLE 9

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

TABLE 7

| | (Mites which damage plants) Tetranychus test | |
|---|---|---|
| Active compounds | Active compound concentration in % | Degree of destruction in % after 2 days |
| (B) | 0.1 | 0 |
| (C) | 0.1 | 0 |
| (A) | 0.1 | 0 |
| (5) | 0.1 | 100 |
| (1) | 0.1 | 100 |
| (4) | 0.1 | 100 |
| (6) | 0.1 | 100 |

It will be appreciated that the instant specification and examples are set forth by way of illustration and not limitation, and that various modifications and changes may be made without departing from the spirit and scope of the present invention.

What we claim is:
1. A carbamate of the formula

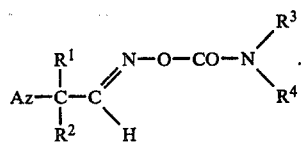

wherein
$R^1$ and $R^2$ each independently is alkyl of 1 to 4 carbon atoms or together form a tetramethylene, pentamethylene or hexamethylene bridge,
$R^3$ is hydrogen or alkyl of 1 to 4 carbon atoms,
$R^4$ is hydrogen, alkyl of 1 to 12 carbon atoms, alkenyl or alkynyl of 2 to 4 carbon atoms, halogenoalkyl with up to 2 carbon atoms and 5 halogen atoms, halogenoalkenyl with up to 3 carbon atoms and 5 halogen atoms, or alkoxyalkyl or alkylthioalkyl with up to 2 carbon atoms in each alkyl moiety, and
Az is pyrazol-1-yl, imidazol triazol-1-yl, indazol-1-yl, benzimidazol-1-yl or benztriazol-1-yl optionally substituted by halogen, alkyl with 1 to 4 carbon atoms, halogenoalkyl with up to 2 carbon atoms and 5 halogen atoms, alkoxy or alkylthio with up to 4 carbon atoms, cyano or nitro.

2. A carbamate according to claim 1, wherein such carbamate is 2-(imidazol-1-yl)-2-methyl-1-methylcarbamoyloximino-propane of the formula

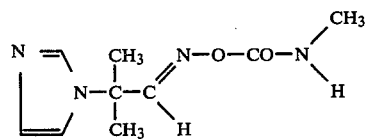

3. A carbamate according to claim 1, wherein such carbamate is 2-(1,2,4-triazol-1-yl)-2-methyl-1-methylcarbamoyloximino-propane of the formula

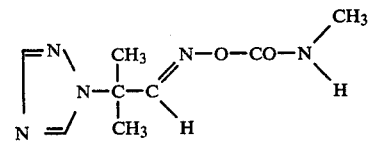

4. A carbamate according to claim 1, wherein such carbamate is 2-(pyrazol-1-yl)-2-methyl-1-methylcarbamoyloximino-propane of the formula

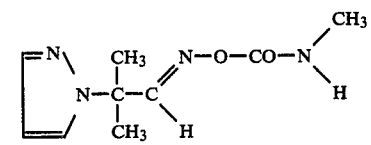

5. A carbamate according to claim 1, wherein such carbamate is 2-(3-methyl-1,2,4-triazol-1-yl)-2-methyl-1-methylcarbamoyloximino-propane of the formula

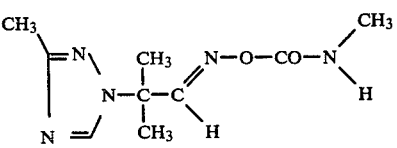

6. A carbamate according to claim 2, wherein such carbamate is 2-(3-methylmercapto-1,2,4-triazol-1-yl)-2-methyl-1-methylcarbamoyloximino-propane of the formula

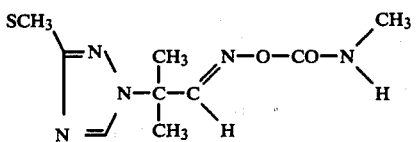

7. An arthropodicidal or nematicidal composition containing as active ingredient an arthropodicidally or nematicidally effective amount of a compound according to claim 1 in admixture with a diluent.

8. A method of combating arthropods or nematodes which comprises applying to the arthropods or nematodes, or to a habitat thereof, an arthropodicidally or nematicidally effective amount of a compound according to claim 1.

9. The method according to claim 8 in which said compound is
2-(imidazol-1-yl)-2-methyl-1-methylcarbamoyloximino-propane,
2-(1,2,4-triazol-1-yl)-2-methyl-1-methylcarbamoyloximino-propane,
2-(pyrazol-1-yl)-2-methyl-1-methylcarbamoyloximino-propane,
2-(3-methyl-1,2,4-triazol-1-yl)-2-methyl-1-methylcarbamoyloximino-propane or
2-(3-methylmercapto-1,2,4-triazol-1-yl)-2-methyl-1-methylcarbamoyloximino-propane.

* * * * *